US00PP30210P2

(12) United States Plant Patent
Bradford et al.

(10) Patent No.: US PP30,210 P2
(45) Date of Patent: Feb. 19, 2019

(54) PLUM TREE NAMED 'PLUMSWEET XXI'

(50) Latin Name: *Prunus salicina*
Varietal Denomination: Plumsweet XXI

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/732,745

(22) Filed: Dec. 26, 2017

(51) Int. Cl.
*A01H 5/08* (2018.01)

(52) U.S. Cl.
USPC ..... Plt./184

(58) Field of Classification Search
USPC ..... Plt./180, 184
See application file for complete search history.

(56) References Cited

U.S. PATENT DOCUMENTS

PP19,591 P2 12/2008 Bradford
PP28,441 P3 9/2017 Bradford

*Primary Examiner* — Susan McCormick Ewoldt

(57) ABSTRACT

The present invention relates to a plum tree and more particularly to a new and distinct variety broadly characterized by a small size, medium vigorous, hardy, and very productive tree. Being self-unfruitful, the present variety requires cross pollination from an apricot, interspecific, or plum that blooms during the late season, such as 'Plumred VII' interspecific tree (U.S. Plant Pat. No. 23,688). The present variety produces a heavy amount of bloom with a moderate amount of pollen to entice good bee activity to facilitate pollination. The fruit matures under the ecological conditions described during the last part of September, with first picking on Sep. 25, 2017, and will hang on the tree an additional thirty days. The fruit is uniformly medium in size, dark purplish red in skin color, dark red in flesh color, clingstone in type, mostly ovate in shape, firm in texture, very sweet, and outstanding in flavor.

1 Drawing Sheet

Botanical classification: *Prunus salicina.*
Varietal denomination: 'PLUMSWEET XXI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'Plumsweet XXI'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2010 one such house containing 'Plumred X' interspecific tree (U.S. Plant Pat. No. 19,591) was crossed by us in this manner. To pollinate this interspecific tree, we selected bouquets from several sources of plum trees without keeping specific written details. Upon reaching maturity the fruit from this interspecific tree was harvested, and the seeds were removed, cracked, stratified and germinated as a group with the label "H8". They were grown as seedlings on their own root in our greenhouse and upon reaching dormancy transplanted to a cultivated area of our experimental orchard located near Le Grand, Calif. in Merced County (San Joaquin Valley). During the summer of 2014 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Plumred X' interspecific tree (U.S. Plant Pat. No. 19,591), by being self-unfruitful and by producing fruit that is clingstone in type, red in flesh color, mostly dark red in skin color, firm, juicy, and very sweet, but is distinguished therefrom by having a smaller size tree, by blooming in the late instead of mid season, and by producing fruit that is smaller in size, that is ovate instead of globose in shape, and that matures about thirty days later.

The present variety is most similar to 'Blackred XXI' plum tree (U.S. Plant Pat. No. 28,441) by being self-unfruitful, by blooming in the late season, and by producing fruit that is clingstone in type, medium in size, firm, juicy, and very sweet, but is distinguished therefrom by having a smaller size tree and by producing fruit that is darker red in flesh color, that is mostly dark red instead of black in skin color, that is ovate instead of oblate in shape, and that matures about thirty days later.

SUMMARY OF VARIETY

The present plum variety is characterized by a small size, medium vigorous, hardy, and very productive tree. Being self-unfruitful, the present variety requires cross pollination from an apricot, interspecific, or plum that blooms during the late season, such as 'Plumred VII' interspecific tree (U.S. Plant Pat. No. 23,688). The present variety produces a heavy amount of bloom with a moderate amount of pollen to entice good bee activity to facilitate pollination. The fruit matures under the ecological conditions described during the last part of September, with first picking on Sep. 25, 2017, and will hang on the tree an additional thirty days. The fruit is uniformly medium in size, dark purplish red in skin color, dark red in flesh color, clingstone in type, mostly ovate in shape, firm in texture, very sweet, and outstanding in flavor.

DRAWING

The accompanying photograph consists of four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of shipping ripe on Sep. 25, 2017, on the original tree during its seventh growing season. The flower and bud descriptions were developed during the previous blooming season. All major color code designations are by reference to the Inter-Society Color Council, National Bureau of Standards. Common color names are also used occasionally.

PARENTAGE

Seed parent: 'Plumred X' (U.S. Plant Pat. No. 19,591) interspecific tree.

Pollen parent: Unknown.

TREE

Size: Small, reaching a height of 8' [2.44 m.] and a spread of 6' [1.83 m.] after seven growing seasons utilizing typical dormant pruning.

Vigor: Medium vigor, responding about average to irrigation and fertilization. The variety grows about 2' [0.61 m.] of surplus top-growth during the spring and summer. The plant should be grown on a standard commercial rootstock for production purposes.

Growth: Upright and moderately dense.

Form: Pruned to a central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid to late seasonal blooming apricot, interspecific, or plum, such as 'Plumred VII' (U.S. Plant Pat. No. 23,688) interspecific tree.

Bearing: Regular bearer, weather dependent, with no crop failures observed as of yet.

Leaf bud burst: Medium, toward the middle of flowering.

Trunk:

*Size*.—Slender to medium, reaching a maximum diameter of 2" [50.8 mm.] after the seventh growing season.

*Texture*.—Medium shaggy.

*Bark color*.—A Moderate yellowish brown [77. m.yBr] and Deep yellowish brown [75. deep yBr] variegation with Grayish brown [61. gy.Br] crevices present.

*Lenticels*.—Approximate Number Per Square Inch: 8. Color: Moderate yellowish brown [77. m.yBr]. Average Size: ¼" [6.4 mm.] in length. The width is typically one fourth as much as the length. Shape: Eye-shaped.

Branches:

*Size*.—Slender, diameter of the scaffold is 1¼" [31.8 mm.] measured 12" above the lowest hanger, the maximum diameter of the lowest hanger is 1" [25.4 mm.].

*Texture*.—Smooth on first and second year wood, increasing in roughness with age.

*Color*.—1st Year Wood Topside: Grayish red [19. gy.R]. 1st Year Wood Underside: Brilliant yellow green [116. brill.YG]. 2nd Year Wood: Light grayish brown [60. l.gy.Br]. Older Wood: A Grayish brown [61. gy.Br] and Dark brown [59. d.Br] variegation with Strong brown [55. s.Br] crevices present.

*Lenticels*.—Number Per Square Inch: About 35 on second year wood. Color: Light grayish brown [60. l.gy.Br]. Average Size: Small, 1/32" [0.8 mm.] in length. The width is typically one fourth as much as the length. Shape: Eye-shaped.

Leaves:

*Size*.—Small. Average Length: 2⅞" [73.0 mm.]. Average Width: 1⅛" [28.6 mm.].

*Arrangement*.—Alternate.

*Thickness*.—Medium.

*Form*.—Elliptical.

*Apex*.—Acuminate.

*Base*.—Acute with an average base angle of 75 degrees.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: ½" [12.7 mm.]. Average Thickness: 1/16" [1.6 mm.]. Color: Strong reddish brown [40. s.rBr].

*Stipules*.—Number: Usually 2 per leaf, up to 6 per growing tip. Average Length: ¼" [6.4 mm.]. Color: Light yellow green [119. l.YG] becoming Moderate reddish brown [43. m.rBr] with age.

*Glands*.—Number: Usually 2 to 4 per leaf. Position: Usually alternate, positioned near the intersection of the petiole and the leaf blade. Form: Globose. Size: Medium, ⅛" [0.5 mm.] in diameter. Color: Brilliant yellow green [116. brill.YG] becoming Grayish reddish brown [46. gy.rBr] with age. Leaf buds: Pointed.

Flower buds:

*Hardiness*.—Hardy with respect to central California blooming season.

*Diameter*.—Typically 3/16" [4.8 mm.] 1 week before bloom.
*Length*.—Typically 3/8" [9.5 mm.] 1 week before bloom.
*Form*.—Not appressed.
*Surface*.—Slightly pubescent.
*Tip color*.—Pale pink [7. p.Pk].

Flowers: Perfect, complete, perigynous, usually a single pistil, typically thirty or more stamens, five sepals and petal locations alternately positioned.
*Average flower diameter*.—1 1/16" [27.0 mm.].
*Average flower depth*.—3/8" [9.5 mm.] when fully open.
*Average pedicel length*.—3/8" [9.5 mm.].
*Number of petals*.—Five, no double blossoms observed.
*Petal arrangement*.—Overlapping.
*Petal shape*.—Oval to circular.
*Petal margin*.—Entire, slightly wavy.
*Average petal diameter*.—1/2" [12.7 mm.].
*Average petal length*.—9/16" [14.3 mm.].
*Petal apex*.—Rounded.
*Petal base*.—Obtuse.
*Petal color*.—White [263. White] on the inside, Pinkish white [9. pkWhite] on the outside.
*Anther color*.—Vivid yellow [82. v.Y].
*Pollen production*.—Moderate, average enticement to bees.
*Pollen color*.—Strong yellow [84. s.Y].
*Stigma color*.—Brilliant greenish yellow [98. brill.gY].
*Stigma position*.—Located about even with the surrounding anthers.
*Ovary*.—Non-pubescent.
*Sepal color*.—Brilliant yellow green [116. brill.YG] on both sides.
*Sepal outer surface*.—Slightly pubescent.
*Sepal length*.—7/32" [5.6 mm.].
*Sepal width*.—1/8" [3.2 mm.].
*Sepal apex*.—Acute, with an average angle of 60 degrees.
*Sepal margin*.—Lightly serrate.
*Average pistil length*.—9/16" [14.3 mm.].
*Average stamen length*.—1/2" [12.7 mm.].
*Stamen position*.—Typically located about 1/32" [0.8 mm.] below the petals.
*Fragrance*.—Moderate.
*Blooming period*.—Late, about seven days after 'Santa Rosa' plum (unpatented).
*Onset of bloom*.—One percent on Feb. 20, 2017.
*Date of full bloom*.—Mar. 1, 2017.
*Duration of bloom*.—One to two weeks, dependent on ambient temperature.
*Bloom density*.—Heavy.
*Number per cluster*.—2 to 7.

FRUIT

Maturity when described: Shipping ripe, Sep. 25, 2017.
Date of first picking: Sep. 25, 2017.
Date of last picking: Oct. 25, 2017.
Size: Uniform, medium.
*Average diameter axially*.—2 7/8" [73.0 mm.].
*Average diameter across cheek plane*.—2 7/16" [61.9 mm.].
*Average diameter across suture plane*.—2 7/16" [61.9 mm.].
*Typical weight*.—5.3 ounces [150 grams].
Form: Mostly uniform, ovate, symmetrical.
*Longitudinal section form*.—Ovate.
*Transverse section through diameter*.—Round.
Suture: A shallow groove extending from the base just to the apex.
Ventral surface: Rounded, lipped slightly on both sides.
Lips: Equal.
Cavity: Flaring, slightly elongated in suture plane, suture showing on one side.
*Depth*.—3/8" [9.5 mm.].
*Breadth*.—1 1/8" [28.6 mm.].
*Stem markings*.—Usually not present.
Base: Truncate, cordate if viewed parallel to the suture.
Apex: Mammiform.
Pistil point: An inconspicuous Pale yellow [89. p.Y] dot.
Stem: Medium.
*Average length*.—11/16" [17.5 mm.].
*Average width*.—1/8" [3.2 mm.].
Skin:
*Thickness*.—Medium.
*Surface*.—Smooth.
*Tenacity*.—Tenacious to the flesh.
*Astringency*.—Moderate.
*Tendency to crack*.—None observed.
*Color*.—A Very deep purplish red [260. v.d.pR] with very heavy Moderate greenish Yellow [102. m.gY] freckling throughout.
*Lenticels*.—Number Per Square Inch: About 200. Average diameter: 1/100" [0.25 mm].
*Bloom*.—Moderate to heavy.
Flesh:
*Color*.—Very dark red [17. v.d.R] near the skin smoothly blending to Deep reddish orange [36. Deep rO] toward the stone with Strong red [12. s.R] fibers throughout.
*Surface of pit cavity*.—Covered with Dark red [16. d.R] fibers.
*Amygdalin*.—Scarce.
*Juice*.—Abundant.
*Texture*.—Genetically melting, but remains firm and crisp through the harvest period.
*Fibers*.—Abundant, fine, tender.
*Ripens*.—Fairly evenly.
*Flavor*.—A tasty balance of acid and sugar, typically 22 brix.
*Aroma*.—Wanting.
*Eating quality*.—Outstanding.

STONE

Type: Clingstone.
Form: Oval.
Hilum: Narrow, oval.
Base: Truncate.
Apex: Rounded.
Sides: Mostly equal.
Surface: Fairly smooth with rounded ridges toward the base.
External color of stone: Brownish orange [54. brO] when first removed.
Pit wall color when cracked: Light yellowish brown [76. l.yBr].
Cavity surface color: Strong yellowish brown [74. s.yBr].
Average pit wall thickness: 1/8" [3.2 mm.].
Average length: 7/8" [22.2 mm.].

Average width: ⅝" [15.9 mm.].
Average breadth: ¼" [6.4 mm.].
Tendency to split: None observed.
Kernel:

*Form*.—Oval.
*Skin color*.—Dark orange yellow [72. d.OY].
*Pellicle color*.—Light orange yellow [70. l.OY].
*Vein color*.—Moderate yellowish brown [77. m.yBr].
*Taste*.—Bitter.
*Viable*.—Yes.
*Average length*.—½" [12.7 mm.].
*Average width*.—⅜" [9.5 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Blackred XXI' plum tree (U.S. Plant Pat. No. 28,441) by being self-unfruitful, by blooming in the late season, and by producing fruit that is clingstone in type, medium in size, firm, juicy, and very sweet, but is distinguished therefrom by having a smaller size tree and by producing fruit that is darker red in flesh color, that is mostly dark red instead of black in skin color, that is ovate instead of oblate in shape, and that matures about thirty days later.

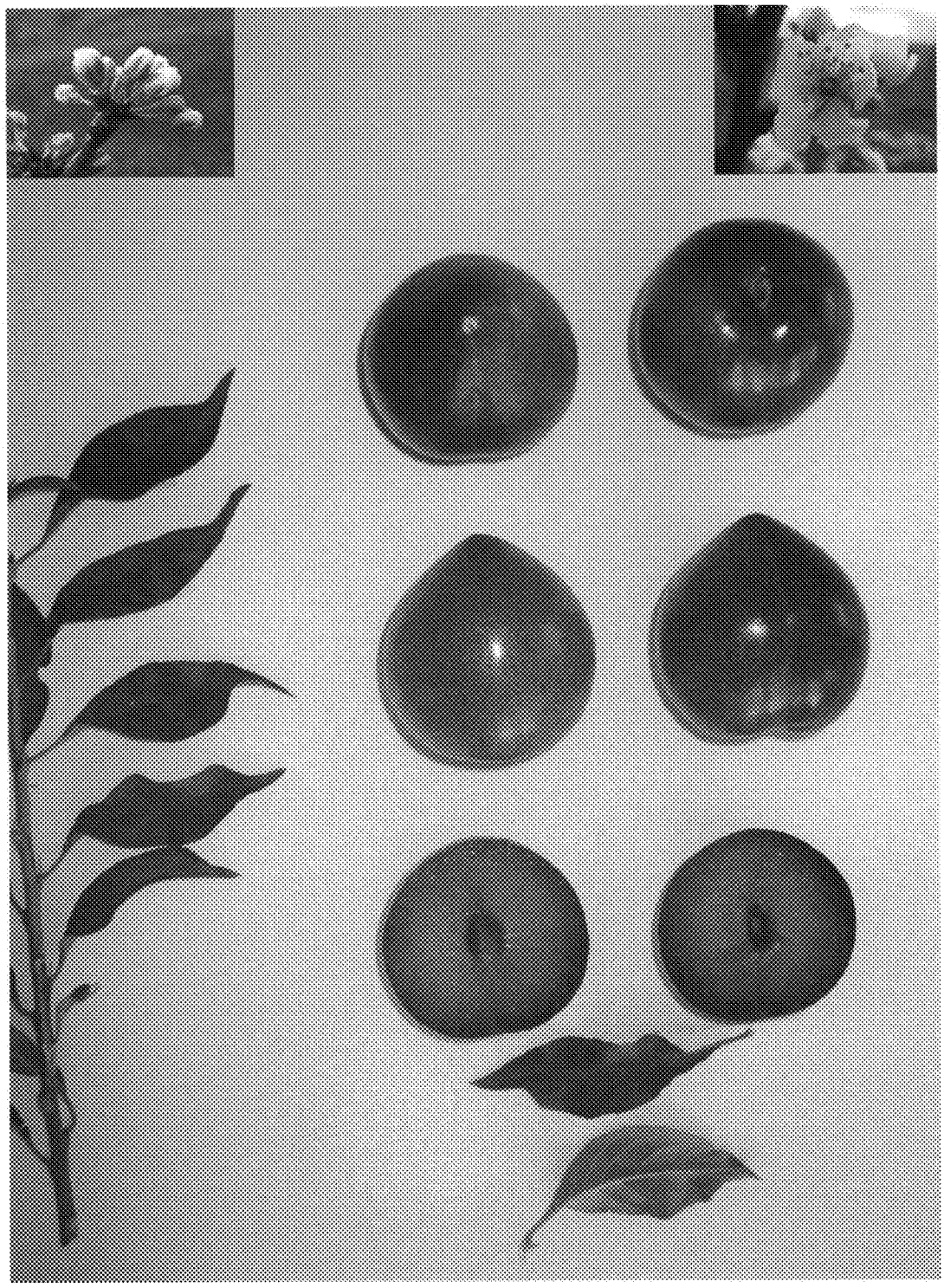

* * * * *